(12) United States Patent
Kasdan et al.

(10) Patent No.: US 6,424,415 B1
(45) Date of Patent: Jul. 23, 2002

(54) METHOD AND APPARATUS FOR VERIFYING UNIFORM FLOW OF A FLUID SAMPLE THROUGH A FLOW CELL AND DISTRIBUTION ON A SLIDE

(75) Inventors: Harvey Kasdan, Van Nuys; Jaehyl Ko, San Diego, both of CA (US)

(73) Assignee: International Remote Imaging Systems, Inc., Chatsworth, CA (US)

( * ) Notice: Subject to any disclaimer, the term of this patent is extended or adjusted under 35 U.S.C. 154(b) by 0 days.

(21) Appl. No.: 09/632,091

(22) Filed: Aug. 2, 2000

Related U.S. Application Data

(62) Division of application No. 08/852,519, filed on May 7, 1997, now Pat. No. 6,184,978
(60) Provisional application No. 60/017,747, filed on May 15, 1996.

(51) Int. Cl.⁷ .............................................. G01N 33/48
(52) U.S. Cl. ......................... 356/246; 356/335; 377/10
(58) Field of Search .......................... 356/246, 39, 73, 356/335–343; 377/10, 11; 436/10, 8, 16; 382/199, 203, 201, 204, 205; 250/573, 574, 576; 73/861.05, 861.11

(56) References Cited

U.S. PATENT DOCUMENTS

| | | | |
|---|---|---|---|
| 4,338,024 A | 7/1982 | Bolz et al. | 356/23 |
| 4,393,466 A * | 7/1983 | Deindoerfer et al. | 356/335 |
| 4,519,087 A | 5/1985 | Deindoerfer | 377/10 |
| 4,612,614 A | 9/1986 | Deindoerfer | 364/415 |
| 4,653,078 A * | 3/1987 | Aritomi et al. | 377/10 |
| 4,696,183 A | 9/1987 | Mitsumaki et al. | 73/19 |
| 4,766,373 A * | 8/1988 | Chambers et al. | 73/861.05 |
| 4,804,267 A * | 2/1989 | Greenfield | 356/335 |
| 5,625,709 A | 4/1997 | Kasdan | 382/203 |
| 5,721,433 A * | 2/1998 | Kosaka | 250/573 |
| 5,728,582 A * | 3/1998 | Taki et al. | 436/10 |
| 6,184,978 B1 * | 2/2001 | Kasdan et al. | 356/246 |

OTHER PUBLICATIONS

*Harvey Lee Kasdan, "Nonparametric Pattern Recognition", A dissertation submitted in partial satisfaction of the requirements for the degree Doctor of Philosophy in Engineering, University of Los Angeles, 1971, pp. 74–77, 201, 214–221.

* cited by examiner

Primary Examiner—Hoa Q. Pham
(74) Attorney, Agent, or Firm—Gray Cary Ware & Freidenrich LLP

(57) ABSTRACT

Particles in a fluid are counted as the fluid flows through an examination area of a particle analyzer. Parameters based upon the particle count are calculated. It is determined whether the at least one calculated parameter is within an allowable range for the parameter. Based on this determination, an indication is provided of uniformity of the fluid sample in the examination area.

14 Claims, 10 Drawing Sheets

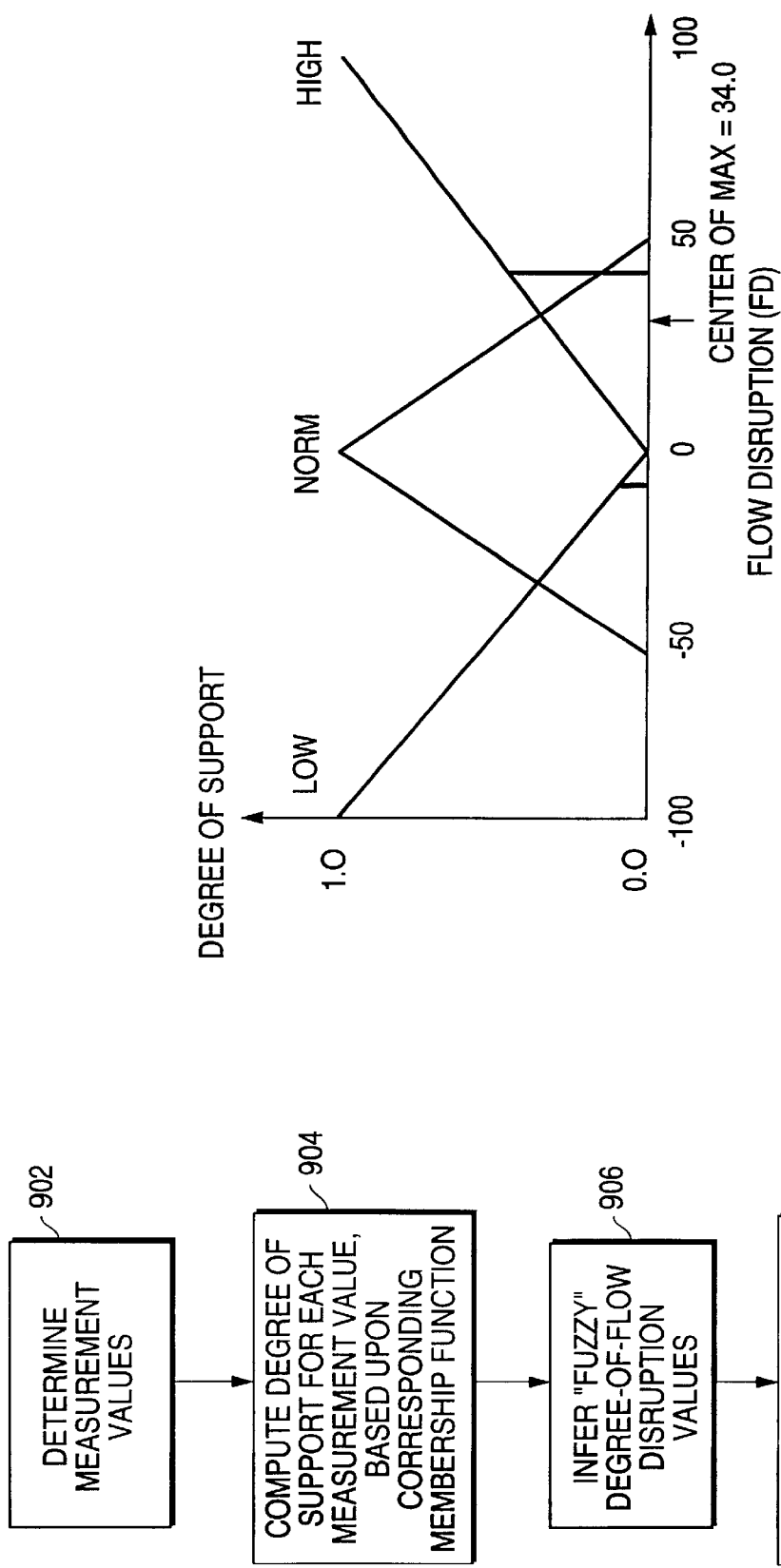

METHOD AND APPARATUS FOR VERIFYING UNIFORM FLOW OF A FLUID SAMPLE THROUGH A FLOW CELL AND DISTRIBUTION ON A SLIDE

This is a divisional application of application No. 08/852,519, filed on May 7, 1997, now U.S. Pat. 6,184,978 which is a provisional application of application No. 60/017,747, filed on May 15, 1996.

TECHNICAL FIELD

The present invention relates to fluid samples in flow cells and distributed on slides and, in particular, to a method for verifying that a fluid sample is flowing uniformly through the flow cell and is uniformly distributed on the slide.

BACKGROUND

A conventional flow cell and particle analyzer is shown, in plan view, in FIG. 1, and a particle analyzer is shown in block schematic form in FIG. 2. The flow cell and particle analyzer automate the job of counting fluid particles suspended in a biological sample (for example, blood cells suspended in a serum sample or particles suspended in a urine sample). More generally, the flow cell and particle analyzer may be used to automate the job of counting any "particles of interest" that are suspended in a fluid sample.

Referring now to FIG. 1, the flow cell includes a body 10 containing a flow chamber having an inlet 12 through which the fluid sample is provided. The flow chamber also has an outlet 14. A passageway 16 extends between the inlet 12 and the outlet 14 such that the fluid sample provided at the inlet 12 flows past an examination area 18 (shown by a dashed line in FIG. 1) and is discharged out of the passageway 16 via the outlet 14.

During a sampling run, the fluid sample is surrounded on both sides by sheath fluid (e.g., saline solution) introduced into the passageway 16 from inlets 13a and 13b. A strobe light 32 (FIG. 2) illuminates the examination area 180 from below and a microscope 30 is focused on the examination area 18 from above. A CCD camera 34 receives the output of the microscope 30 to form a series of still frame images.

In particular, a frame grabber 40 "grabs" the still frame images and stores them in a memory. A CPU 56 combines selected components of the still frame images to generate composite images which represent the particles in multiple images. Thus, individual particles (for example, different types of blood cells) can be analyzed and sorted.

In order for the particle analyzer to perform reliably, the fluid sample having the suspended particles of interest must flow uniformly through the flow cell examination area 18, without interruption. Even if interruptions occur relatively infrequently, when they do occur they will cause the determined particle counts to be inaccurate.

SUMMARY

In accordance with one embodiment of the invention, a particle analyzer verifies the uniformity of fluid flow through a flow cell examination area without reference to particles of interest (that may or may not be suspended therein). First, the particle analyzer inspects still frame images generated by a frame grabber of the flow cell and the light level in the examination area is determined. Then, a heavy stain is injected into the flow cell. Thereafter, the particle analyzer inspects further still frame images generated by the frame grabber of the flow cell and determines from the further images whether there is a uniformly decreased intensity in light level in the examination area (corresponding to the heavy stain flowing through the examination area). If so, then the flow of fluid through the flow cell examination area is indicated as being uniform. Otherwise, the flow of fluid through the flow cell examination area is indicated as being non-uniform.

In accordance with another embodiment of the invention, a particle analyzer executes statistical tests on counts of particles of interest in the fluid sample under analysis and uses these counts to determine whether the fluid sample is flowing uniformly past an examination area of the fluid particle analyzer. In particular, statistical parameters of the particle counts are calculated. Then, it is determined whether the calculated statistical parameters are within an allowable range for the parameters. Based on this determination, an indication is provided of whether the fluid sample is flowing uniformly past the examination area.

A better understanding of the features and advantages of the invention will be obtained by reference to the following detailed description and accompanying drawings which set forth an illustrative embodiment in which the principles of the invention are utilized.

BRIEF DESCRIPTION OF THE FIGURES

FIG. 9 is a flowchart which illustrates a process in accordance with a fourth embodiment of the invention for determining whether fluid is flowing smoothly past the examination area of the apparatus of FIG. 1.

FIG. 17 is an example of a membership function for computing a defuzzified value, FD(Center of Maxes), in step 908 of the flowchart of FIG. 9.

DETAILED DESCRIPTION

Figure 1:
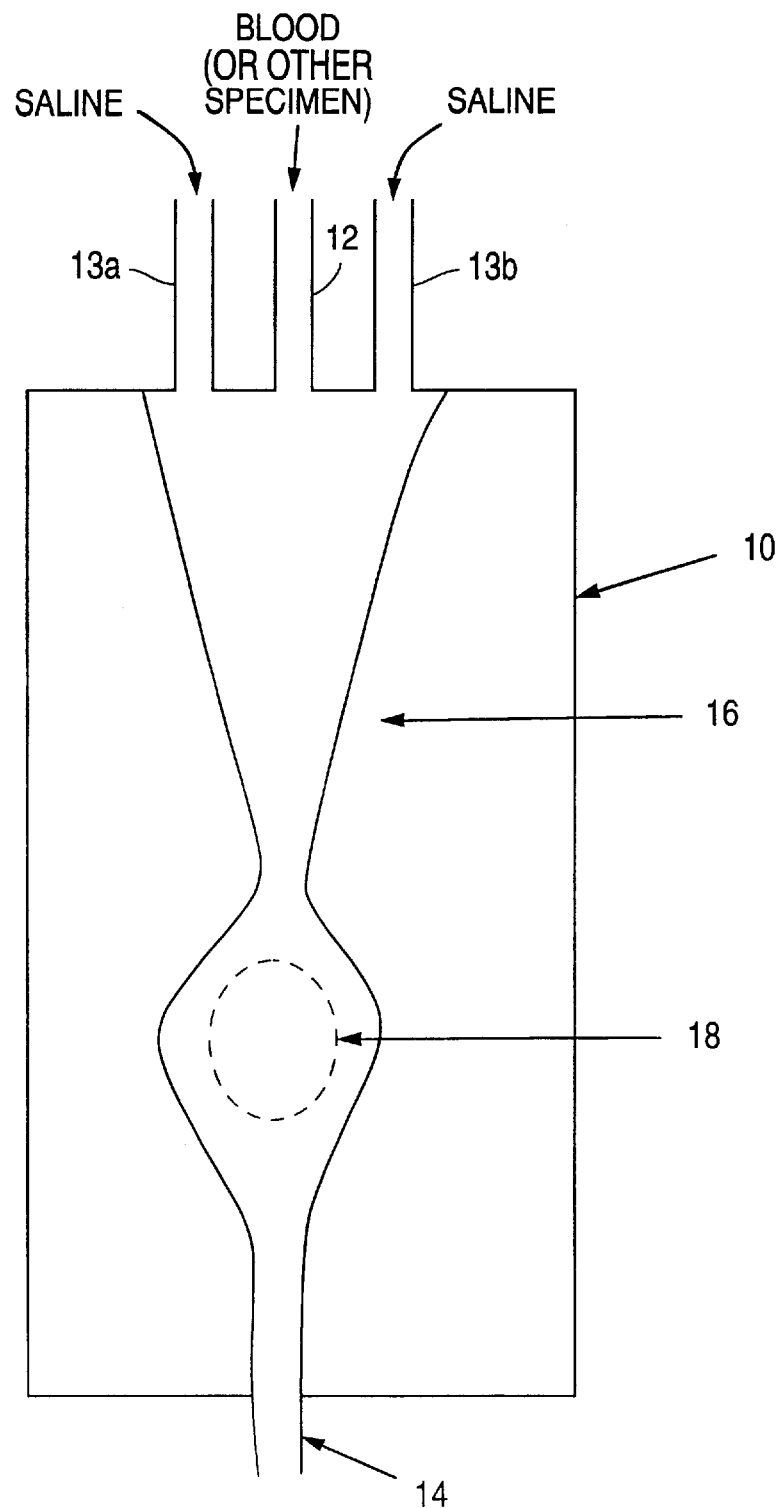
FIG. 1 is a plan view of a flow cell for moving a fluid sample past an examination area.
Figure 2:
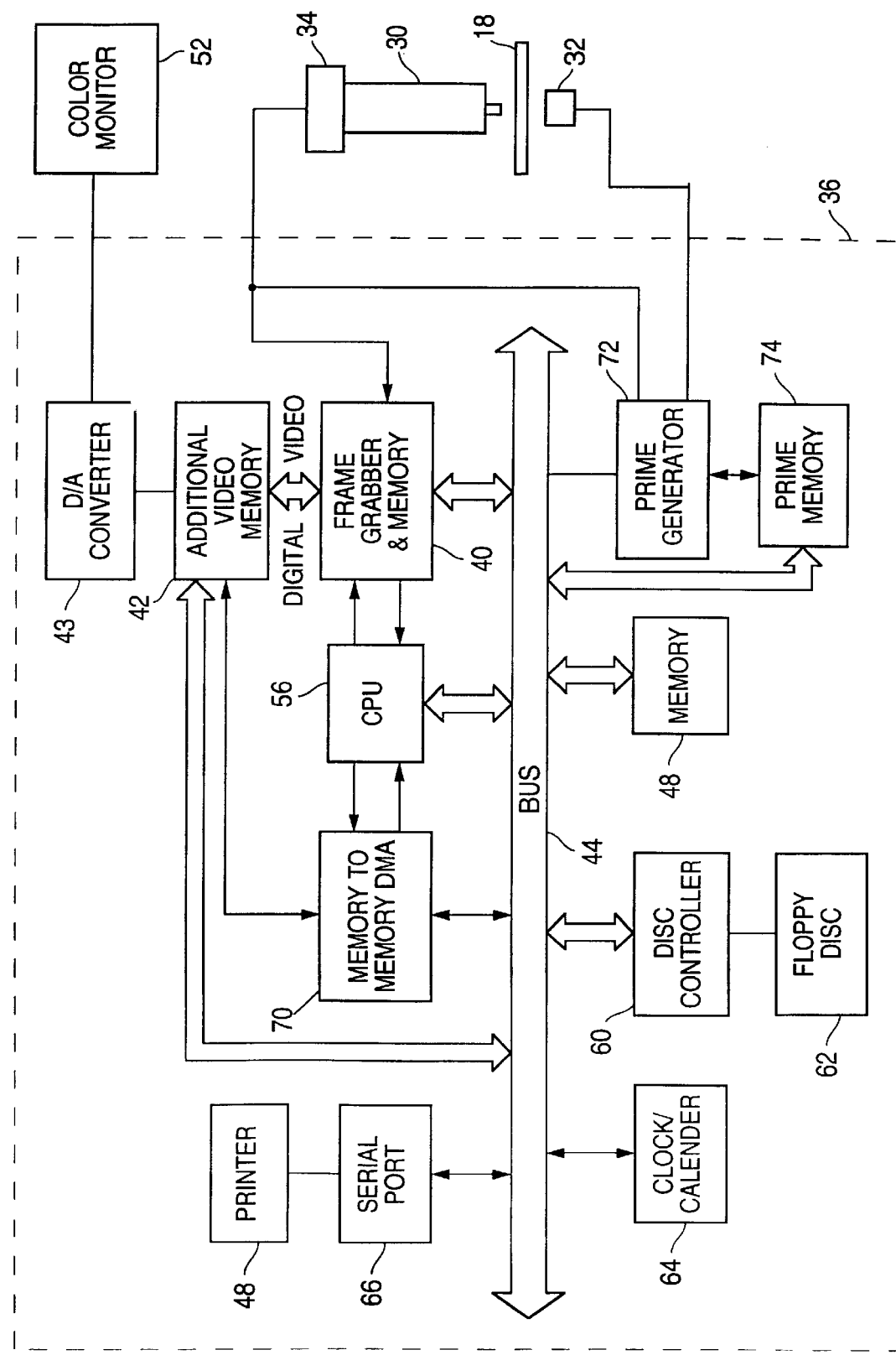
FIG. 2 is a schematic block diagram of a particle analyzer for use with the flow cell of FIG. 1 in practicing the present invention.
Figure 3:
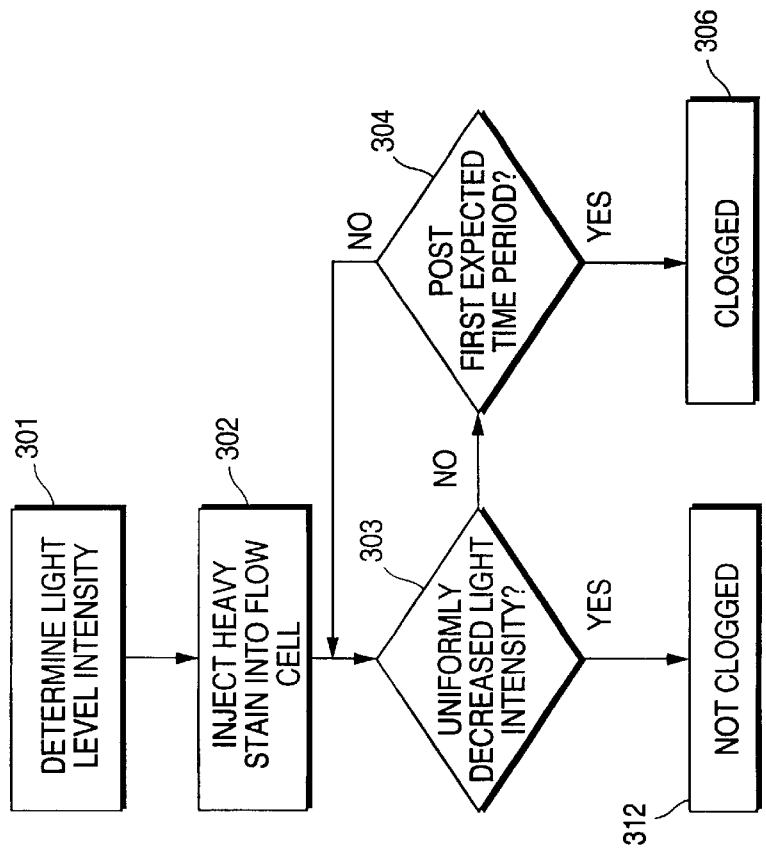
FIG. 3 is a flowchart which illustrates a process in accordance with a first embodiment of the invention for determining whether a fluid sample is flowing uniformly past an examination area of the apparatus of FIG. 1.

A first embodiment of the present invention is now described with reference to the flow chart in FIG. 3. The steps illustrated in the flowchart of FIG. 3 are executed by the processor 36 of the flow analyzer shown in FIG. 2. At step 301, when it is desired to determine whether fluid is flowing uniformly past an examination area of a flow cell (such as the examination area 18 of the flow cell shown in FIG. 1), the processor determines an average light level intensity of the examination area (or of a portion of the examination area). Preferably, the average light intensity is measured by averaging the intensity of all portions, of more than one still frame image, that correspond to the examination area. However, while not as reliable, it is within the scope of the invention to determine the light level intensity by considering only a representative portion of each still frame image (or even of only one still frame image). Then, at step 302, a heavy stain is caused to be injected into the flow cell. For example, the heavy stain may be provided at the inlet 12 of the FIG. 1 flow cell. The heavy stain may be provided concurrently with a fluid sample under analysis, provided that the stain is not so opaque that it interferes with the ability of the particle analyzer to distinguish particles in the fluid sample under analysis. Alternately, the heavy stain may be provided exclusive of a fluid sample under analysis (e.g., at the end of a sample run).

After injecting the stain into the flow cell, at step 303, the particle analyzer looks for a period of uniformly decreased light level intensity in the still frame images, as measured in the direction perpendicular to the fluid flow. At step 304, if the uniformly decreased light level intensity was expected to be seen within a first time period since injection of the stain into the flow cell, and the first time period has passed, then, at step 306, it is reported that fluid is not flowing uniformly past the examination area 18 of the flow cell.

Otherwise, if the period of uniformly decreased light level intensity is seen within the first time period, then, at step 312, it is reported that the fluid is flowing uniformly past the examination area 18 of the flow cell.

Figure 5:
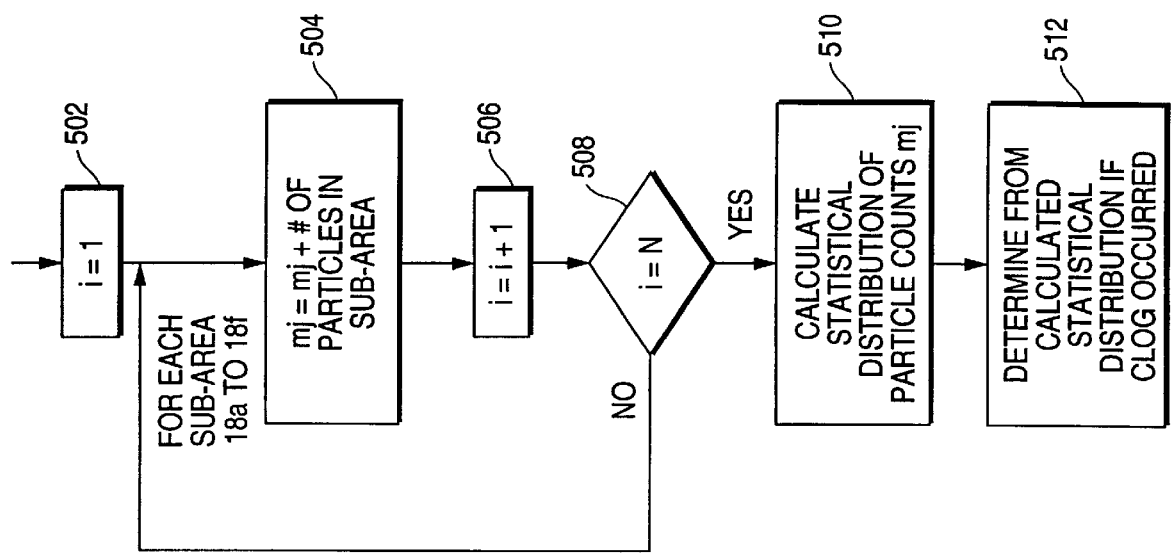
FIG. 5 is a flowchart which illustrates a process in accordance with a second embodiment of the invention for determining whether fluid is flowing uniformly past the examination area of the apparatus of FIG. 1.
Figure 4:
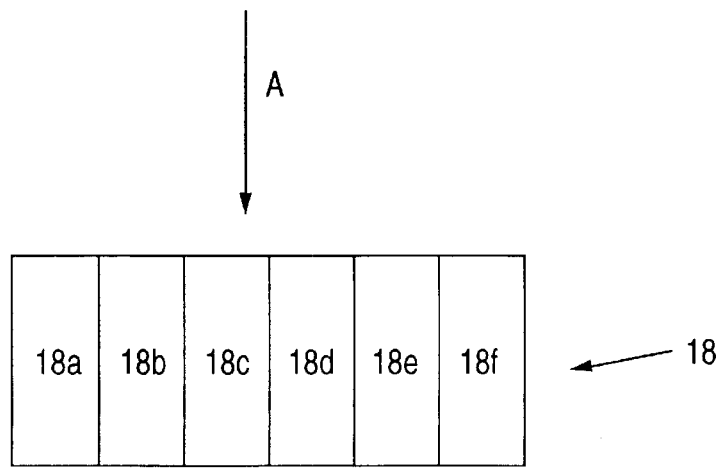
FIG. 4 is a top view of the examination area of the flow cell of FIG. 1.

In accordance with a second embodiment of the invention, the examination area 18 is logically divided into sub-areas 18a through 18f, perpendicular to the direction of fluid flow, as shown in FIG. 4. The direction of fluid flow is shown in FIG. 4 by an arrow A. FIG. 5 illustrates the flow of the basic process executed by the processor 36 in accordance with the second embodiment of the invention. At step 502, the processor 36 initializes an index variable "i". Then, at each execution of step 504, for the current frame grabbed by the frame grabber 40, the processor 36 determines a count of the number of particles "of interest" in each sub-area 18a through 18f of the examination area 18 and accumulates this count for all grabbed frames thus far processed. (The particles that are "of interest" are the particles that the particle analyzer is designed to detect and analyze.) For example, if the particle analyzer is a blood cell analyzer, the particles "of interest" may be red blood cells. Alternately, the "particles of interest" may be calibrator particles which have been added to a fluid sample for volume calibration of the particles that the particle analyzer is designed to detect and analyze.

The processor 36 increments the index variable "i" at step 506. Once a predetermined number of frames have been processed, as indicated by "i" being equal to "n" at step 508, the processor 36 proceeds (at step 510) to calculate a statistical distribution of the number of particles counted in the sub-areas 18a through 18f. Then, at step 512, the processor 36 determines from the calculated statistical distribution the fluid flow uniformity within the examination area 18.

Figure 6:
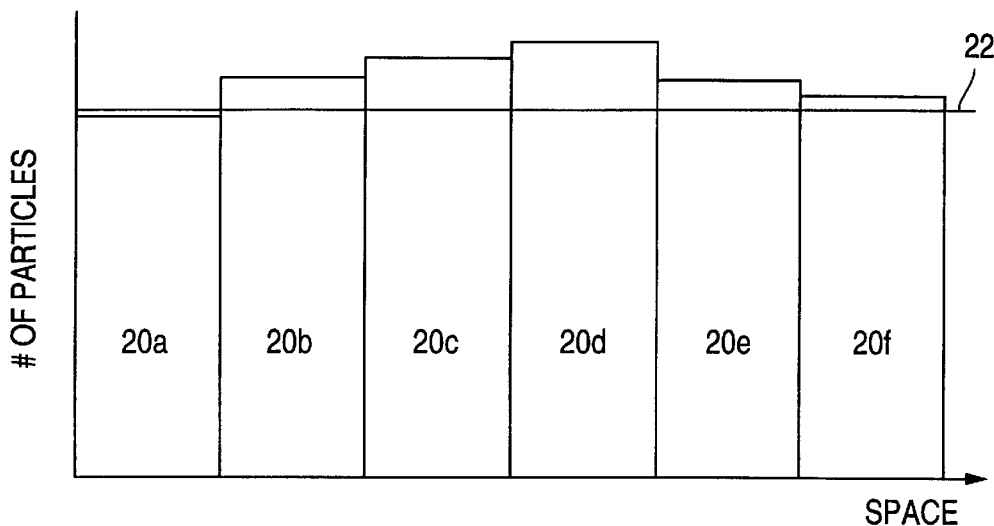
FIG. 6 is a bar graph which illustrates how the determining step 512 may be carried out in the process illustrated in FIG. 5.

FIG. 6 is a bar graph whose bars 20a through 20f represent the accumulated counts of the number of the particles in the sub-areas 18a through 18f. The curve 22 in FIG. 6 represents an expected distribution of particles in the sub-areas 18a through 18f if fluid is flowing uniformly past the examination area 18. Generally, a uniform distribution (or some other expected distribution determined by fluid dynamics) of particles is expected. If the distribution of accumulated counts as represented by bars 20a through 20f in FIG. 6 is within an allowable range of the expected distribution as represented by curve 22, then the processor 36 determines that the fluid is flowing uniformly past the examination area 18. On the other hand, if the distribution of accumulated counts is outside the allowable range, then the processor 36 determines that fluid is not flowing uniformly past the examination area 18.

Figure 7:
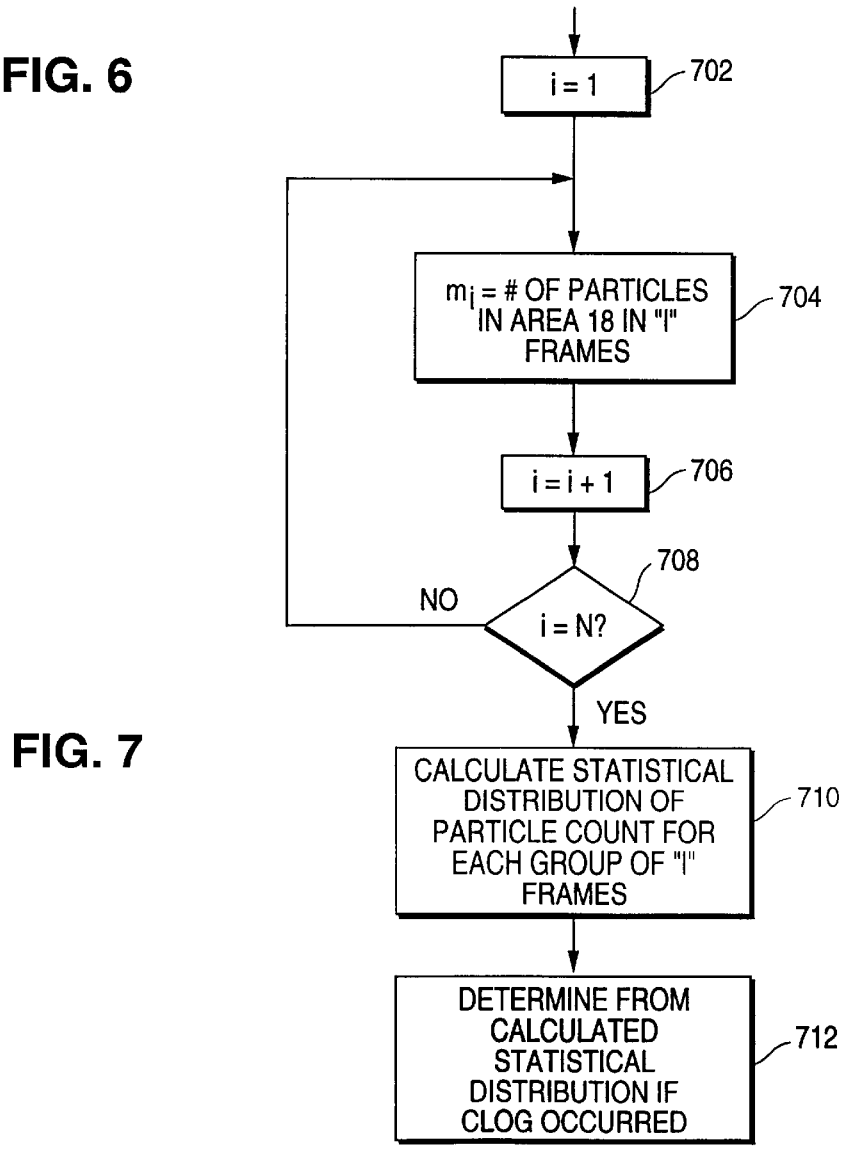
FIG. 7 is a flowchart which illustrates a process in accordance with a third embodiment of the invention for determining whether fluid is flowing smoothly past the examination area of the apparatus of FIG. 1.

In accordance with a third embodiment of the invention, counts of particles of interest are accumulated during specified time periods, and the processor 36 calculates statistical parameters of the accumulated counts. Thus, it can be seen that the third embodiment of the invention is "time-oriented", in contrast to the second embodiment of the invention which is "space-oriented". FIG. 7 illustrates the flow of the basic process executed by the processor 36 in accordance with the third embodiment of the invention. At step 702, the processor 36 initializes an index variable "i". Then, for each group of "1" frames (e.g., 50 frames, where each frame represents sampling at different times) grabbed by the frame grabber 40, the processor 36 sets a count variable, indexed by "i", to the number of sample particles counted in those frames (step 704). The processor 36 increments the index variable "i" at step 706. Once the sample particles have been counted in each of "n" groups of "1" frames (as determined at step 708), the processor 36 proceeds (at step 710) to calculate a statistical distribution of the number of sample particles counted in the groups of "1" frames. Then, at step 712, the processor 36 determines from the calculated statistical distribution if fluid has flown uniformly past the examination area 18 during the sample run.

Figure 8:
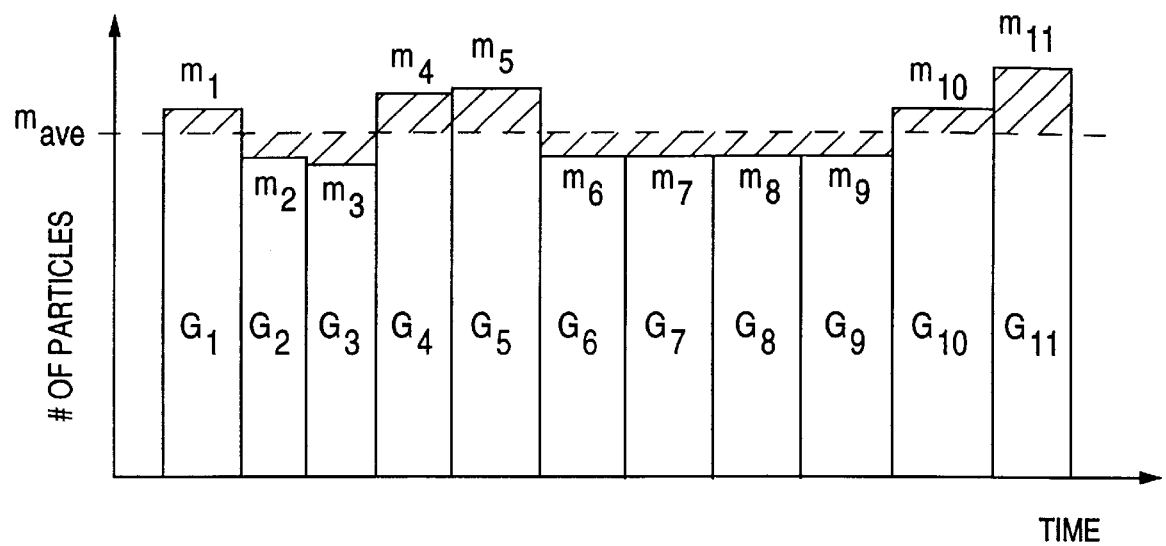
FIG. 8 is a bar graph which illustrates how the determination step may be carried out in the process illustrated in FIG. 7.

A first aspect of the third embodiment of the invention is now discussed with reference to the bargraph shown in FIG. 8. FIG. 8 shows a bargraph of an example of sample particle counts for each of "n" (in the example of FIG. 8, n=11) groups, $G_1, G_2, \ldots, G_n$ of "1" frames (e.g., 50 frames). The height of each bar $m_1, m_2, \ldots, m_n$ indicates the number of sample particles counted for the corresponding group of "1" frames. The dotted line labelled $m_{ave}$ indicates an overall mean number of sample particles, calculated by the processor 36 at step 610, for each group of "1" frames over the "n" groups. Also at step 710, the processor 36 determines, for each group of "1" frames, how far the overall mean number of particles, $m_{ave}$, per group of "1" frames differs from the actual count, $m_j$, of sample particles in each group of "1" frames. This difference is shown graphically in FIG. 8 by a hatch pattern. Then, at step 712, the processor determines if the differences are within an allowable range. If the differences are within the allowable range, the processor 36 indicates that the fluid sample is flowing uniformly past the examination area 18.

In accordance with a second aspect of the third embodiment of the invention, the processor 36 calculates, at step 710, a parameter $$x = \Sigma i * m_i, \ i=1 \text{ TO } n \tag{1}$$

assuming that x defines a weighted sum of Poisson random variables. Then, at step 712, the processor 36 determines if "x" is within an allowable range.

In accordance with a third aspect of the third embodiment of the invention, at step 710, the processor 36 calculates a parameter $$x = \frac{\sum m_i}{n}, i = 1 \text{ TO } N \qquad (2)$$

where x is the average number of particles counted in each group of "1" frames". The processor 36 then calculates a parameter $$y = \Sigma |m_i - x|, i = 1 \text{ TO } N \qquad (3)$$

Since $|m_i-x|$ indicates how much the particle count for an individual group of "1" frames deviates from the overall average, y indicates the sum of the deviations for the individual groups. Then, at step 712, the processor 36 determines if the parameter y is within some allowable range. The parameter y being within the allowable range indicates, within some degree of statistical certainty, that the fluid sample is flowing uniformly past the examination area 18.

In accordance with still further aspects according to the third embodiment of the invention, the examination area 18 is logically divided by the processor 36 into the sub-examination areas 18a to 18f (FIG. 4). The processor 36 executes the process shown in steps 702–712 of the FIG. 7 flowchart for each sub-examination area 18a to 18f.

For example, in accordance with a fourth aspect of the third embodiment, at step 710, the processor 36 calculates the statistical parameter x, as shown above in equation (1), for each of the areas 18a to 18f. Then, at step 712, the processor 36 determines whether the x calculated for each area 18a to 18f is within an allowable range. In accordance with a fifth aspect of the third embodiment, at step 710, the processor 35 calculates the statistical parameters x and y, shown above in equations (2) and (3), for each of the areas 18a to 18f. Then, at step 712, the processor 36 determines whether the y calculated for each area 18a to 18f is within an allowable range.

Alternately, and particularly for situations where processing power is at a premium, at step 710, the processor 36 calculates the statistical parameters from counts of particles in only one or more selected ones of the areas 18a to 18f. At step 712, the processor 36 determines whether the calculated statistical parameters, for the selected areas, are within an allowable range. It is noted that this embodiment may not be as reliable as embodiments which utilize the entire examination area 18.

In accordance with a further embodiment of the invention, values are obtained of several measurements, where each measurement is at least partially indicative of the flow of the fluid sample through the flow cell. Then, these partial indications are combined to generate a "crisp" indication of the fluid flow. The combining is preferably implemented by the CPU 56 (FIG. 2) executing special purpose software or firmware.

One relatively simple way to combine the partial indications is to use a linear discriminant function, in which the partial indications are each multiplied by a weighting factor (indicative of the contribution of the measurement) to generate a weighted partial indication. The weighted partial indications are summed together and compared to a threshold to produce the "crisp" indication of the fluid flow.

Another way to combine the partial indications is to use "fuzzy logic". Such a fuzzy logic method is advantageous for use with an automated particle analyzer, which is normally unattended. The method preferably implemented by the CPU 56 (FIG. 2) executing special purpose software.

FIG. 9 is a flowchart illustrating an embodiment of the fuzzy logic detection method. At step 902, the fuzzy logic detection method obtains values of the several measurements (measurement values) that are at least partially indicative of the flow of the fluid sample through the examination area of the flow cell. At step 904, for each of degrees of flow 1, 2 and 3 (e.g., clog, partial clog and no clog), a degree of support for each measurement value is determined from a membership function of the measurement. At step 906, values indicating the degree of support are provided to inference machines or rule functions, which calculate "fuzzy" degree of flow disruption values. Then, at step 908, calculated degree of flow disruption values are defuzzified to a "crisp" number to determine whether a flow disruption has occurred.

Figure 10:
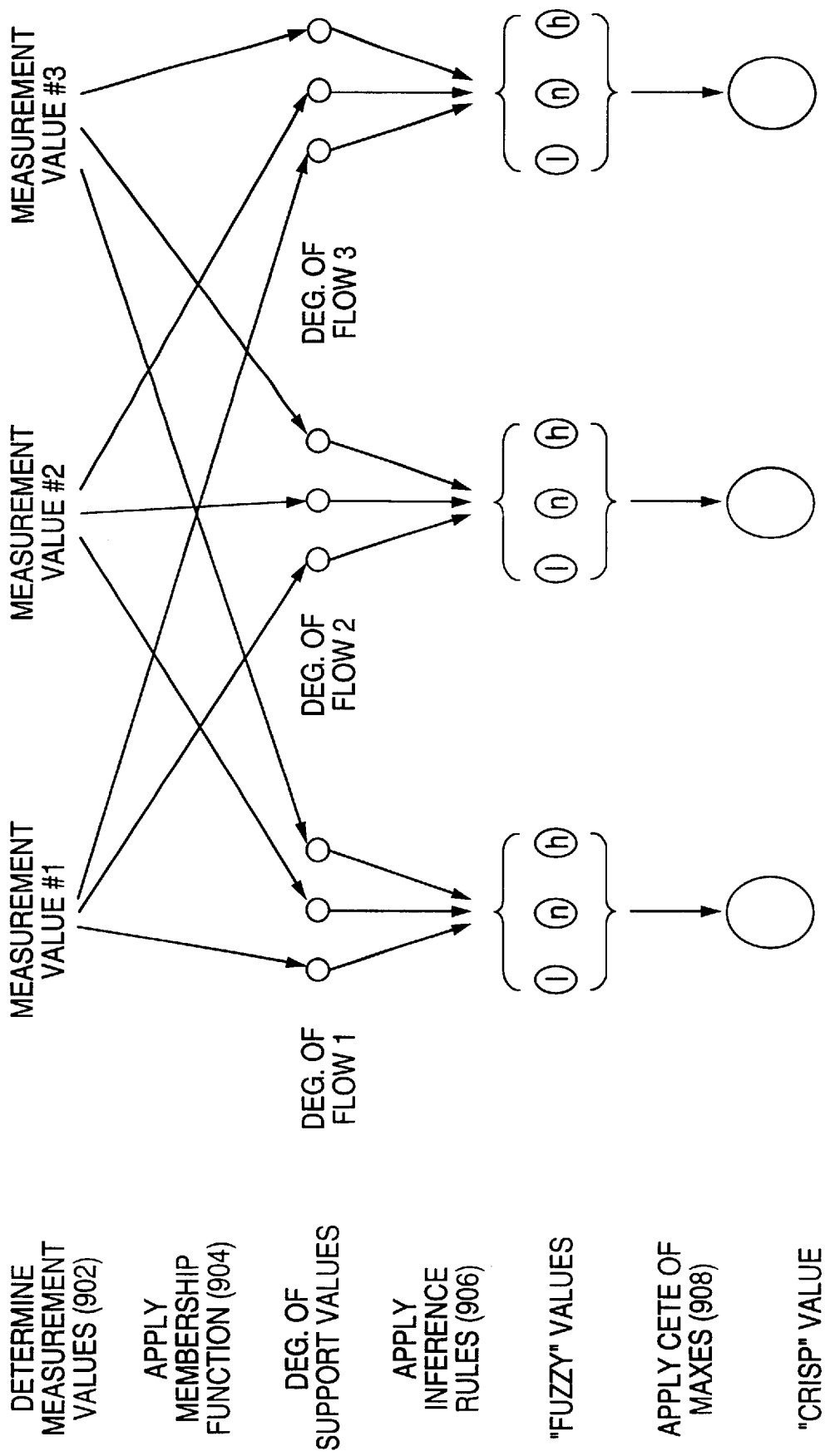
FIG. 10 is a illustrates the data flow of the process shown in the flowchart of FIG. 9.

The following terms, defined below, are employed in describing the fuzzy logic detection method in accordance with an embodiment of the invention.

linguistic variable or measurement
  a linguistic description, parameter or metric related to an event or control input (e.g. temperature)
terms
  ranked linguistic descriptions of a measurement. E.g., temperature {low, normal, high}
degree of support
  degree to which a measurement is a member of the term; normalized to a number between 0 and 1
membership function
  a function that yields its degree of support given a measurement value
inference machine
  rules of the fuzzy logic
defuzzification
  a process of converting "fuzzy" values to a "crisp" and real value The fuzzy logic embodiment is now discussed in more detail with reference to the data flow diagram shown in FIG. 10. First, for each of one or more degrees of flow (e.g., "no clog", "partial clog" and "full clog"—shown as degree of flow 1, 2 and 3 in FIG. 10) of the fluid in the flow cell, a degree of support value for each measurement value is computed from the membership function for the measurement (step 904). To determine the membership function for a measurement, a number of sample runs are carried out and measurement values determined. Meanwhile, an operator observes the runs and determines for each run which of the one or more degrees of flow occurred. Then, the determinations of which degree of flow occurred are correlated to the measurement values to determine the membership function for each measurement. That is, a membership function for a particular measurement provides a numeric indicator of association of each of one or more linguistic descriptions of flow occurrence (e.g., no clog, partial clog and full clog) with a particular measurement value.

Next, the computed degree-of-support values for each degree-of-flow are provided to an inference machine for that degree of flow. The inference machine calculates degree-of-flow disruption "fuzzy" values (step 906). For example, the inference machine may calculate "fuzzy" values CLOG[low], CLOG[norm] and CLOG[high] for each degree of flow where each represents a numeric indicator of an association (low association, normal association, and high association, respectively) that the particular degree of flow is the actual degree of flow.

Next, for each degree of flow, the "fuzzy values" CLOG[low], CLOG[norm] and CLOG[high] are "defuzzified" into a crisp prediction of whether the fluid sample is flowing through the flow cell with that degree of flow (step 908).

An example of the parameters, the terms of measurements and the graphical representation of the membership functions are now described. The "critical" points of each term are determined statistically, in advance, using the mean and standard deviation, and it is the critical points that determine the membership function for the parameter.

For example, approximately 1000 observed samples may be classified into three groups: no-clog, some-clog and full-clog. The mean and standard deviation of the measurements for each group of samples are then calculated. Then, either one or two standard deviations are added to determine a range of each term.

Stain Measurement (ST)

When it is desired to determine whether the flow cell is clogged (e.g., at the end of a particular specimen analysis run), additional stain is injected into the flow cell. Then, the light intensity of subsequently grabbed still frame images is measured. If the flow cell is completely clogged, there will be no discernable difference in light reading before and after the additional stain is injected into the flow cell. Thus, the measured intensity is then translated into a numerical measure of association of whether the flow cell is clogged (true indicating a greater association of the numeric value with the condition that the flow cell is clogged and false indicating a greater association with the condition that the flow cell is not clogged).

Temporal Flow Variance (TFV)

Figure 11:
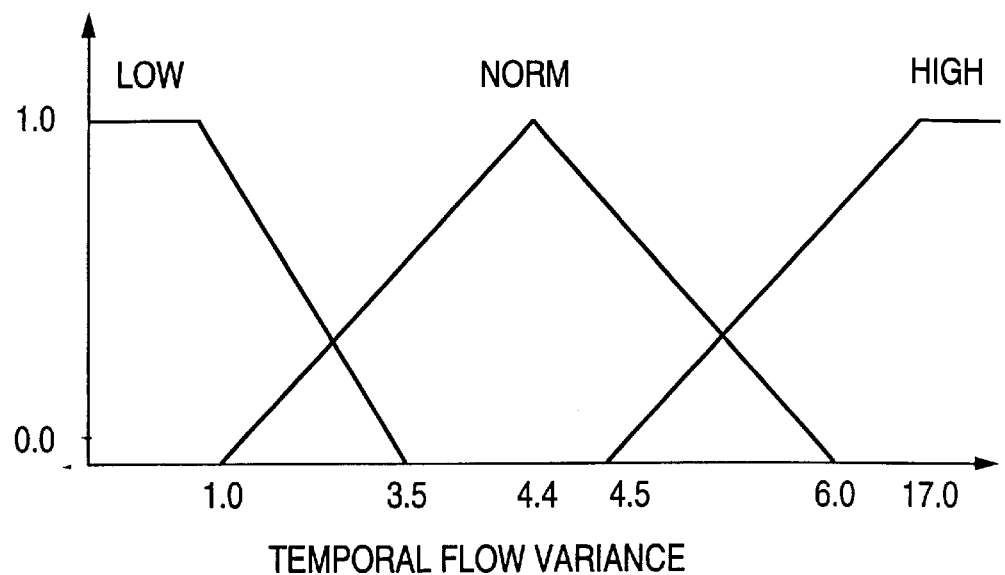
FIGS. 11–16 are examples of membership functions for computing a degree of support for various measurement values in step 904 of the flowchart of FIG. 9.

The TFV measures the variance of the flow rate from frame to frame, or from group of frames to group of frames. For example, in one embodiment, the frames are grouped into about 10 bins and the number of analytes in each bin are counted. These counts/bins are then used to calculate Tnorm, a Poisson distribution based parameter. If there are a sufficient number of analytes in each frame, then the TFV can be calculated on an individual frame basis. Example set measurement functions for TFV are shown in FIG. 11.

Spatial Flow Variance (SFV) Measurement

Figure 12:
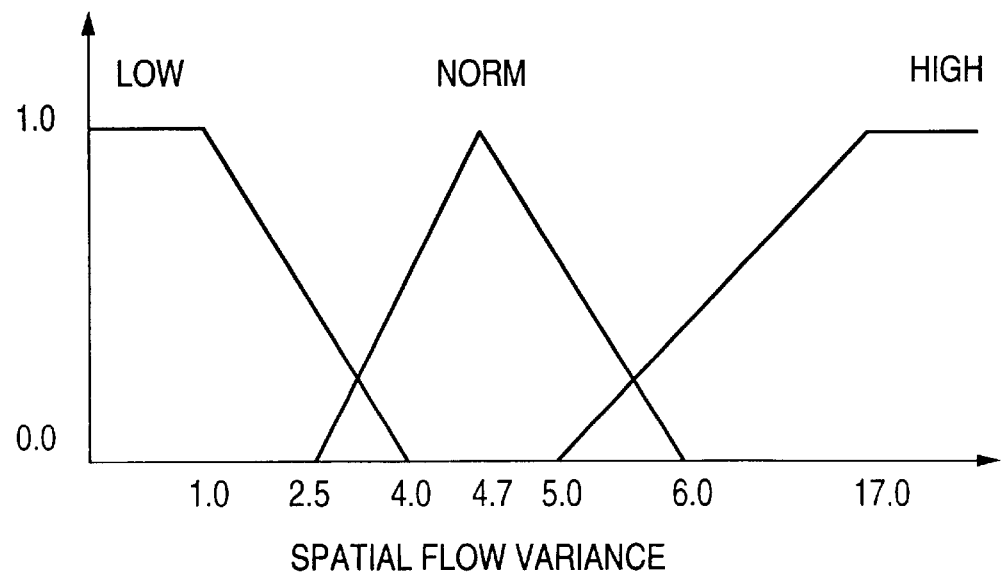

The SFV provides an indication of a variance of distribution of particles of interest in a direction perpendicular to the direction of fluid flow in the flow cell. As described above with respect to FIG. 4, the examination area is equally divided into a number of sub-areas (18a through 18f in FIG. 4) and the particles of interest (analytes) in each sub-area are accumulated. Then, these accumulated counts are used to calculate Tnorm, a Poisson distribution based parameter. As with TFV discussed above, if there are a sufficient number of analytes in each sub-area of each frame, then the SFV can be calculated on an individual frame basis. Example set measurement functions for SFV are shown in FIG. 12.

Spatial Delta(max-min) Variance (SDV) Measurement

Figure 13:
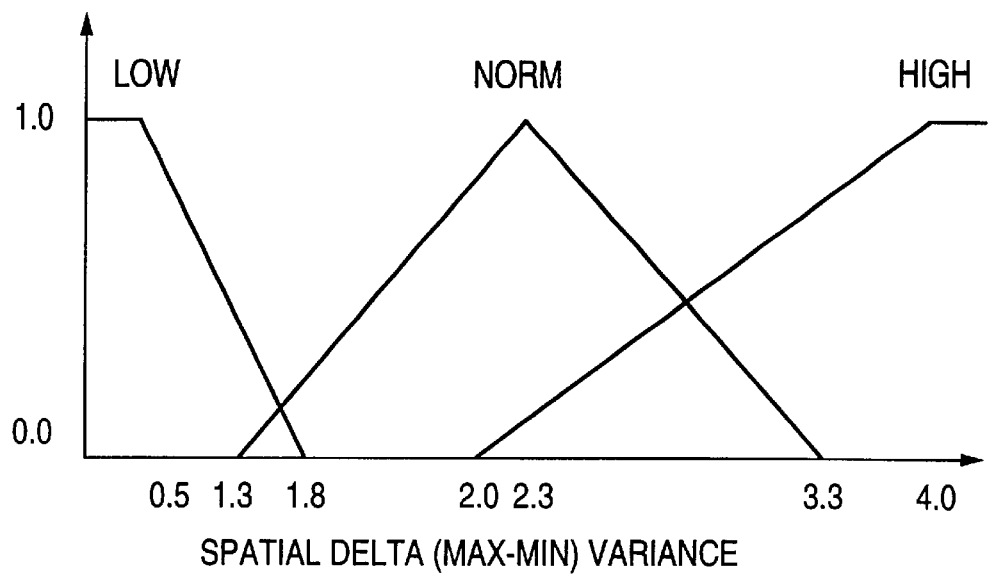

The SDV also provides an indication of a variance of distribution of particles along a direction perpendicular to the direction of fluid flow in the flow cell. The SDV, however, is more sensitive to sharp peaks and valleys in this distribution than is the SFV. The accumulated counts for each sub-area are used to calculate delta=(maximum−minimum)/average. As with TFV and SFV discussed above, if there are a sufficient number of analytes in each sub-area of each frame, then the SDV can be calculated on an individual frame basis. Example set measurement functions for SDV are shown in FIG. 13.

Concentration Ratio of LPF to HPF (CR) Measurement

Figure 14:
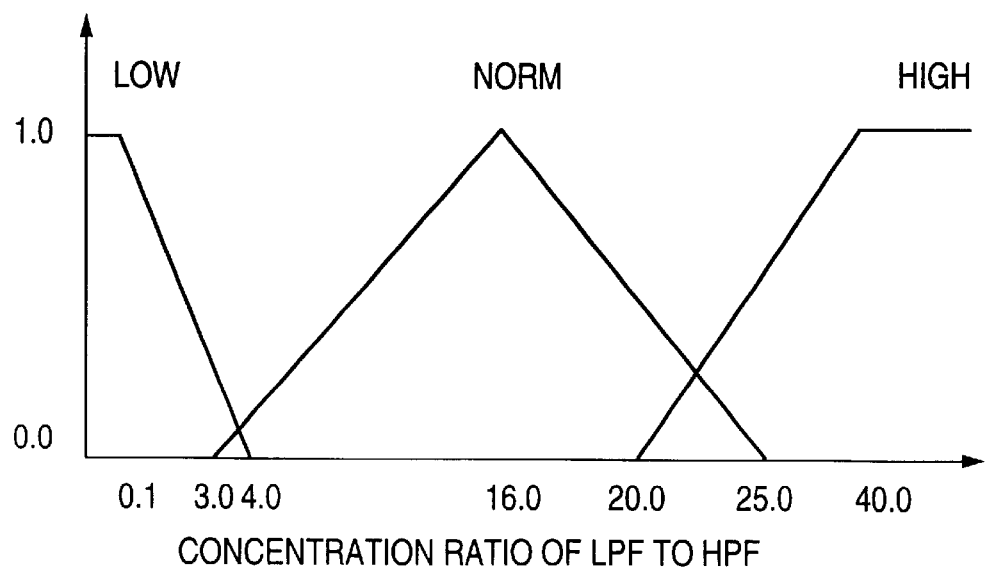

The CR measures the difference in concentration of particles of interest between the low power field and high power field. The concentration of the small particles detected in low power field, designated as size group 4 (LPF4) is divided by the concentration sum of particles in high power size groups 1, 2, 3, and 4, thus excluding the smallest high power group, designated as high power field 5. Theoretically, this value should be about 16. The CR gives an indication of whether a clog occurred between frames grabbed in low power mode of the frame grabber 40 and frames grabbed in high power mode of the frame grabber 40. Example set membership functions for CR are shown in FIG. 14.

LPF4 (<EPI class) Concentration (LPC) Measurement

Figure 15:
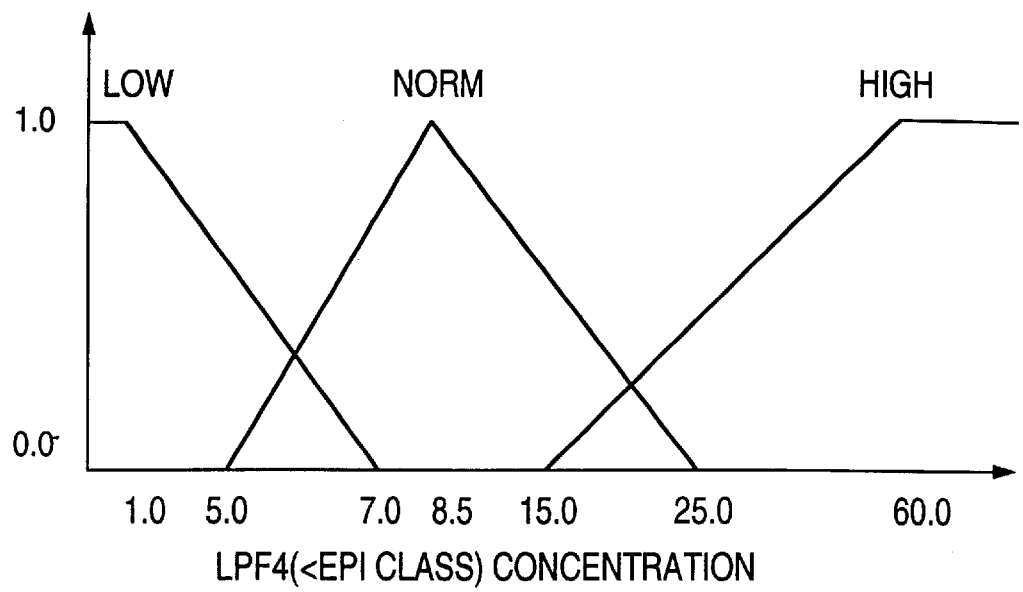

It was empirically determined and reasonable that a high concentration of small particles (e.g., LPF4 class analytes) is associated with a higher probability of the flow cell becoming clogged. Example set measurement functions for LPC are shown in FIG. 15.

Center of Mass Shift Variance (CMS) Measurement

The CMS measures the temporal shift of analytes along the direction perpendicular to fluid flow in the flow cell. The "center of mass" in the direction perpendicular to fluid flow for each sub-area 18a through 18f is calculated. Theoretically, the CMS measurement should be about 127.5 if fluid is flowing perfectly uniformly through the flow cell. The calculated center of mass/frames is then used to calculate Tnorm, a Poisson distribution based parameter.

Center of Mass=(X[1]+X[2]+. . . X[n])./n, where n is equal to the number of analytes and X[i] is equal to x-position of i-th analyte. Again, if there are a sufficient number of analytes in each sub-area of each frame, then the CM can be calculated on an individual frame basis.

Figure 16:
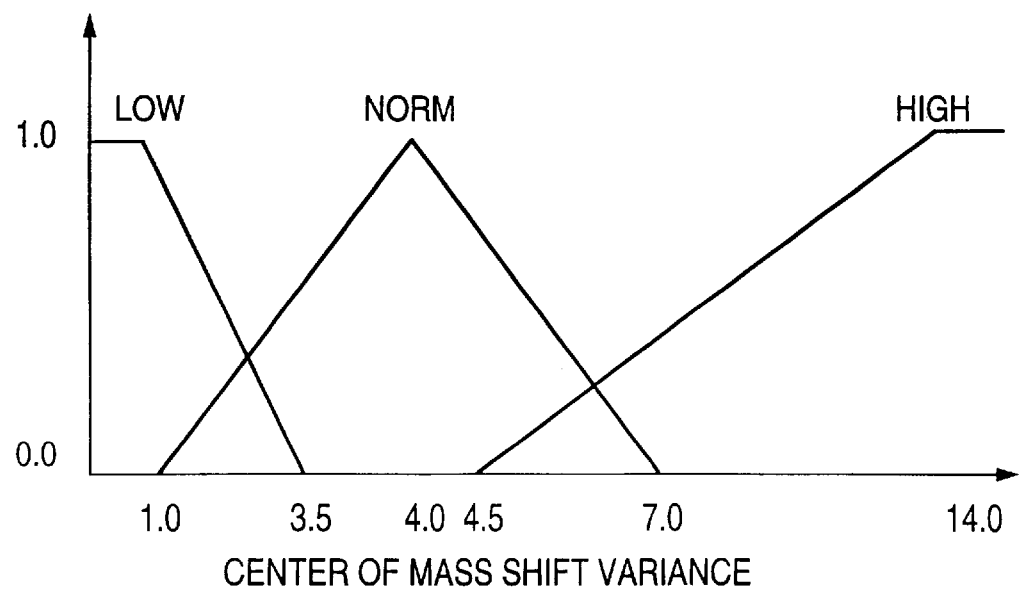

Example set measurement functions for CMS are shown in FIG. 16.

An embodiment of the inference machines is now described.

Full Clog Inference Machine

The measurements provided to the Full Clog Inference Machines are ST, TFV, SFV and SDV.

Step 1: Apply Rules (Inference Rules)

CLOG[low]=(ST[false]+TFV[low]+SFV[low]+SDV[low])/4

CLOG[norm]=min (TFV[norm], SFV[norm], SDV[norm])

CLOG[high]=(ST[true]+TFV[high]+SFV[high]+SDV[high])/4

Step 2: Calculate Final Score (Defuzzification) See FIG. 17 for an example of a membership function for the defuzzified value, FD(Center of Maxes)

FD(low)=−CLOG[low]*100

FD(high)=CLOG[high]*100 if (CLOG[low]<CLOG[high])
    FD(norm)=−(CLOG[norm]*50)+50 else
    FD(norm)=(CLOG[norm]*50)−50
    Weighted Sum=(FD(low)* CLOG[low])+(FD(norm) * CLOG[norm])+(FD(high) * CLOG[high])

FD(Center of Maxes)=Weighted Sum/(CLOG[low]+CLOG[norm]+CLOG[high])

The range of FD(Center of Maxes) is from −100 to 100.

if (FD(Center of Maxes)>20)→Full Clog

Partial Clog Inference Machine

The measurements used in determining Partial Clog are LPC, CMS, CR, TFV, SFV and SDV.

Step 1: Apply Rules (Inference Rules)

Shift Variance (low)=(LPC[low]+CMS[low])/2

Flow Variance (low)=max (CR[norm], TFV[low], SFV[low], SDV[low])

CLOG[low]=(Shift Variance(low)+Flow Variance(low))/2

Shift Variance(norm)=(LPC[norm]+CMS[norm])/2

Flow Variance (norm)=max ( TFV[norm], SFV[norm], SDV[norm])

CLOG[norm]=(Shift Variance(norm)+Flow Variance (norm))/2

Shift Variance(high)=(LPC[high]+CMS[high])/2

Flow Variance(high)=max (max(CR[low], CR[high]), TFV[high], SFV[high], SDV[high])

CLOG[high]=(Shift Variance(high)+Flow Variance (high))/2

Step 2: Calculate Final Score (Defuzzification). Defuzzification is done the same way as the Full Clog fuzzy logic.

if (Center of Max>=25)→Partial Clog

Example

CR=5.02, ST=false, LPC=69.5, CMS=7.6, TFV=3.8, SFV=8.02, SDV=1.94

Step 1: Find Degree of Support from Each Measurement

ST[false]=0.7 ST[true]=0.0

CR[low]=0.0 CR[norm]=0.155 CR[high]=0.0

LPC[low]=0.0 LPC[norm]=0.0 LPC[high]=1.0

CMS[low]=0.0 CMS[norm]=0.0 CMS[high]=0.326

TFV[low]=0.0 TFV[norm]=0.823 TFV[high]=0.0

SFV[low]=0.0 SFV[norm]=0.0 SFV[high]=0.252

SDV[low]=0.0 SDV[norm]=0.641 SDV[high]=0.0

Step 2: Feed into Full Clog Inference Machine

CLOG[low]=0.175 CLOG[norm]=0.0 CLOG[high]=0.063

FD(Center of Maxes)=−11<20, therefore no full clog is inferred.

Step 3: Feed into Partial Clog Inference Machine

CLOG[low]=0.0775 CLOG[norm]=0.411 CLOG[high]=0.458

FD(Center of Maxes)=34>25, therefore partial clog is inferred.

An example is now described.

A. Test Setup

Three sets of data were tested. The 3 sets are GUNKY, LEARNING and TEST. As the name implies the GUNKY set represents samples that are likely to cause clogs in the flow cell. Amorphous specimens, specimens with lots of crystals and specimens with lots of bacteria are examples of the samples which comprise the GUNKY set. The GUNKY set does not represent the population. The LEARNING set, however, is a better representation of the population and more realistic samples. The LEARNING set was used in fine-tuning the fuzzy logic. After fine-tuning the fuzzy logic, it was tested on TEST set. The data are collected from two different flow cell systems. When these samples were run, the operator visually observed the processing of each specimen and classified them into no clog, partial clog and full clog. The Fuzzy Logic was applied to these data sets. The Fuzzy Logic classification was compared to the Operator's classification.

Test Results

The following terms, defined below, are employed in describing the test and results.

True Positive (TP)

Operator reported Clog and Fuzzy Logic yielded Clog

True Negative (TN)

Operator reported No Clog and Fuzzy Logic yielded No Clog

False Positive (FP)

Operator reported No Clog but Fuzzy Logic yielded Clog

False Negative (FN)

Operator reported Clog but Fuzzy Logic yielded No Clog

Sensitivity

TP/(TP+FN)

Specificity

TN/(FP+TN)

Positive Predictive Value (PPV)

TP/(TP+FP)

Negative Predictive Value (NPV)

TN/(TN+FN)

Efficiency (TP+TN)/(TP+FP+FN+TN)

The test results for the Fuzzy Logic classifications are shown in tables below:

TABLE 1

LEARNING Set

|  | Fuzzy: Full Clog | Fuzzy: Partial Clog | Fuzzy: No Clog |
|---|---|---|---|
| Operator: Full Clog | 11 | 0 | 0 |
| Operator: Partial Clog | 1 | 2 | 6 |
| Operator: No Clog | 11 | 8 | 414 |

TABLE 2

LEARNING Set With Positive Full and Partial Clogs Added

|  | Fuzzy: Clog | Fuzzy: No Clog |
|---|---|---|
| Operator: Clog | 14 | 6 |
| Operator: No Clog | 19 | 414 |

TABLE 3

TEST Set

|  | Fuzzy: Full Clog | Fuzzy: Partial Clog | Fuzzy: No Clog |
|---|---|---|---|
| Operator: Full Clog | 13 | 1 | 1 |
| Operator: Partial Clog | 6 | 5 | 6 |
| Operator: No Clog | 23 | 7 | 510 |

TABLE 4

TEST Set With Positive Full and Partial Clogs Added

|  | Fuzzy: Clog | Fuzzy: No Clog |
|---|---|---|
| Operator: Clog | 25 | 7 |
| Operator: No Clog | 30 | 510 |

TABLE 5

GUNKY Set

|  | Fuzzy: Full Clog | Fuzzy: Partial Clog | Fuzzy: No Clog |
|---|---|---|---|
| Operator: Full Clog | 8 | 0 | 1 |
| Operator: Partial Clog | 1 | 5 | 4 |
| Operator: No Clog | 0 | 3 | 31 |

TABLE 6

GUNKY Set With Positive Full and Partial Clogs Added

|  | Fuzzy: Clog | Fuzzy: No Clog |
|---|---|---|
| Operator: Clog | 14 | 5 |
| Operator: No Clog | 3 | 31 |

TABLE 7

All Samples

|  | Fuzzy: Full Clog | Fuzzy: Partial Clog | Fuzzy: No Clog |
|---|---|---|---|
| Operator: Full Clog | 32 | 1 | 2 |
| Operator: Partial Clog | 8 | 12 | 16 |
| Operator: No Clog | 34 | 18 | 955 |

TABLE 8

All Samples With Positive Full and Partial Clogs Added

|  | Fuzzy: Clog | Fuzzy: No Clog |
|---|---|---|
| Operator: Clog | 53 | 18 |
| Operator: No Clog | 52 | 955 |

TABLE 9

Fuzzy Logic Performance

|  | Sensitivity | Specificity | PPV | NPV | Efficiency |
|---|---|---|---|---|---|
| LEARNING | 0.7 | 0.956 | 0.424 | 0.986 | 0.945 |
| TEST | 0.78 | 0.944 | 0.455 | 0.986 | 0.935 |
| GUNKY | 0.77 | 0.912 | 0.824 | 0.861 | 0.849 |
| ALL SAMPLES | 0.747 | 0.948 | 0.505 | 0.982 | 0.935 |

It should be understood that various embodiments of the invention described hereinabove are applicable beyond the area of fluid flow through a flow cell. For example, it is important that particles contained within a fluid on a microscope slide (e.g., presented as a wet mount or as a dry smear), to be examined microscopically, are uniformly distributed throughout an examination area. For example, blood cells in a blood smear should be uniformly distributed over the examination area of the microscope slide. In such an embodiment, fields of the examination area are scanned (and examined in temporal succession) as disclosed, for example, in U.S. Pat. No. 5,625,709 (incorporated herein by reference in its entirety), the particles of these scanned fields are counted, and the counts subjected to the statistical analysis set forth above. In addition, in enhancements of this embodiment, it is determined which particular sub-areas of the examination area have a uniform distribution of particles, and the results of the particle analysis are then based only on these particular sub-areas.

It should be further understood that, while in the described embodiments many of the method steps for determining flow quality are carried out by the CPU 56 executing special purpose firmware or software, it is within the scope of the invention for some or all of the method steps to be performed by hardwired circuitry.

What is claimed is:

1. A method of determining flow quality of a fluid sample, in a particle analyzer, through an examination area of a flow chamber, comprising:

measuring the fluid sample flowing through the examination area of the flow chamber to determine a plurality of measurement values each at least partially indicative of a degree of flow of the fluid sample through the examination area;

combining the measurement values to generate a combined value; and determining the flow quality of the fluid sample responsive to the combined value;

wherein the measuring step includes for each of a plurality of degrees of flow, determining degree of support values for each measurement value by applying a membership function to the measurement value, the membership function applied corresponding to the measurement and the degree of flow, and the degree of support values for a particular degree of flow and for a particular measurement value corresponding to an association of a linguistic description of the particular degree of flow of the fluid sample with the particular measurement value; and wherein the combining step includes for each of the plurality of degrees of flow, determining degree of flow disruption prediction values by applying an inference rule to one or more of the degree of support values determined for the degree of flow, the inference rule corresponding to the degree of flow, and the degree of flow disruption value for each degree of flow corresponding to the association of that particular degree of flow based collectively on the measurement values from which the degree of support values determined for the that particular degree of flow; and for each degree of flow, determining values of a final prediction for the degree of flow by combining the determined degree of flow disruption prediction values for that degree of flow, wherein the final prediction values are the combined value.

2. The method of claim 1, wherein the step of determining valuer of a final prediction for each degree of flow includes:

determining a weighted sum of the determined degree of flow disruption prediction values for the that degree of flow; and determining a center of maxes of the determined degree of flow disruption prediction values in response to a weighted sum of the determined degree of flow prediction values and to a sum of the determined degree of flow prediction values.

3. The method of claim 2, wherein the step of determining a center of maxes includes dividing the weighted sum of the determined degree of flow prediction values by the sum of the determined degree of flow prediction values.

4. The method of claim 1, wherein the step of determining the flow quality of the fluid sample further includes comparing the final prediction values to predetermined ranges of final prediction values.

5. The method of claim 1, wherein the plurality of measurements includes two or more of:

stain measurement;

temporal flow variance;

spatial flow variance;

spatial delta variance;

a comparison of two or more independent measurements of concentration of particles in respective independent size ranges;

concentration of particles having a small size; and center of mass shift variance.

6. A method of determining flow quality of a fluid sample, in a particle analyzer, through an examination area of a flow chamber, comprising:

measuring the fluid sample flowing through the examination area of the flow chamber to determine a plurality of measurement values each at least partially indicative of a degree of flow of the fluid sample through the examination area;

combining the measurement values to generate a combined value; and determining the flow quality of the fluid sample responsive to the combined value;

wherein the step of combining the measurement values to generate a combined value includes:

multiplying functions of each measurement value by a weighting factor to generate a weighted partial indication; and summing the weighted partial indications to generate the combined value.

7. A method of determining flow quality of a fluid sample, in a particle analyzer, through an examination area of a flow chamber, comprising:

measuring the fluid sample flowing through the examination area of the flow chamber to determine a plurality of measurement values each at least partially indicative of a degree of flow of the fluid sample through the examination area;

combining the measurement values to generate a combined value; and determining the flow quality of the fluid sample responsive to the combined value;

wherein the plurality of measurements includes two or more of:

stain measurement;

temporal flow variance;

spatial flow variance;

spatial delta variance;

a comparison of two or more independent measurements of concentration of particles in respective independent size ranges;

concentration of particles having a small size; and center of mass shift variance.

8. A particle analyzer for analyzing a fluid sample including particles suspended therein, comprising:

a flow chamber including an examination area;

measuring means for measuring the fluid sample flowing through the examination area of the flow chamber to determine a plurality of measurement values each at least partially indicative of a degree of flow of the fluid sample through the examination area;

combining means for combining the measurement values to generate a combined value; and determining means for determining the flow quality of the fluid sample responsive to the combined value;

wherein the determining means is first determining means, and wherein the measuring means includes second determining means for, for each of a plurality of degrees of flow, determining degree of support values for each measurement value by applying a membership function to the measurement value, the membership function applied corresponding to the measurement and the degree of flow, and the degree of support values for a particular degree of flow and for a particular measurement value corresponding to an association of a linguistic description of the particular degree of flow of the fluid sample with the particular measurement value; and wherein the combining means includes third determining means for, for each of the plurality of degrees of flow, determining degree of flow disruption prediction values by applying an inference rule to one or more of the degree of support values determined for the degree of flow, the inference rule corresponding to the degree of flow, and the degree of flow disruption value for each degree of flow corresponding to the association of that particular degree of flow based collectively on the measurement values from which the degree of support values determined for the that particular degree of flow; and fourth determining means for, for each degree of flow, determining values of a final prediction for the degree of flow by combining the determined degree of flow disruption prediction values for that degree of flow, wherein the final prediction values are the combined value.

9. The particle analyzer of claim 8, wherein the fourth determining means includes:

fifth determining means for determining a weighted sum of the determined degree of flow disruption prediction values for the that degree of flow; and sixth determining means for determining a center of maxes of the determined degree of flow disruption prediction values in response to a weighted sum of the determined degree of flow prediction values and to a sum of the determined degree of flow prediction values.

10. The particle analyzer of claim 9, wherein the sixth determining means includes dividing means for dividing the weighted sum of the determined degree of flow prediction values by the sum of the determined degree of flow prediction values.

11. The particle analyzer of claim 8, wherein the first determining means includes comparing means for comparing the final prediction values to predetermined ranges of final prediction values.

12. The particle analyzer of claim 8, wherein the plurality of measurements includes two or more of:

stain measurement;

temporal flow variance;

spatial flow variance;

spatial delta variance;

a comparison of two or more independent measurements of concentration of particles in respective independent size ranges;

concentration of particles having a small size; and center of mass shift variance.

13. A particle analyzer for analyzing a fluid sample including particles suspended therein, comprising:

a flow chamber including an examination area;

measuring means for measuring the fluid sample flowing through the examination area of the flow chamber to determine a plurality of measurement values each at least partially indicative of a degree of flow of the fluid sample through the examination area;

combining means for combining the measurement values to generate a combined value; and determining means for determining the flow quality of the fluid sample responsive to the combined value;

wherein the combining means includes:

multiplying means for multiplying functions of each measurement value by a weighting factor to generate a weighted partial indication; and summing means for summing the weighted partial indications to generate the combined value.

14. A particle analyzer for analyzing a fluid sample including particles suspended therein, comprising:

a flow chamber including an examination area;

measuring means for measuring the fluid sample flowing through the examination area of the flow chamber to determine a plurality of measurement values each at least partially indicative of a degree of flow of the fluid sample through the examination area;

combining means for combining the measurement values to generate a combined value; and determining means for determining the flow quality of the fluid sample responsive to the combined value;

wherein the plurality of measurements includes two or more of:

stain measurement;

temporal flow variance;

spatial flow variance;

spatial delta variance;

a comparison of two or more independent measurements of concentration of particles in respective independent size ranges;

concentration of particles having a small size; and center of mass shift variance.

* * * * *